(12) United States Patent
Sacchetti et al.

(10) Patent No.: US 11,016,081 B2
(45) Date of Patent: *May 25, 2021

(54) APPARATUS, METHOD, SYSTEM FOR THE DETERMINATION OF THE AGGREGATION RATE OF RED BLOOD CELLS

(71) Applicant: Alcor Scientific, Inc., Smithfield, RI (US)

(72) Inventors: Peter Sacchetti, Attleboro, MA (US); Francesco Frappa, Udine (IT)

(73) Assignee: Alcor Scientific Inc., Smithfield, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/691,489

(22) Filed: Nov. 21, 2019

(65) Prior Publication Data
US 2020/0088717 A1 Mar. 19, 2020

Related U.S. Application Data

(63) Continuation of application No. 15/640,852, filed on Jul. 3, 2017, now Pat. No. 10,488,396, which is a
(Continued)

(51) Int. Cl.
| | |
|---|---|
| *C12M 1/42* | (2006.01) |
| *G01N 33/49* | (2006.01) |
| *G01N 21/51* | (2006.01) |
| *G01N 15/05* | (2006.01) |
| *G01N 15/00* | (2006.01) |

(52) U.S. Cl.
CPC ......... *G01N 33/4905* (2013.01); *G01N 15/05* (2013.01); *G01N 21/51* (2013.01);
(Continued)

(58) Field of Classification Search
CPC ...................................................... C12M 1/42
See application file for complete search history.

(56) References Cited

U.S. PATENT DOCUMENTS

| | | |
|---|---|---|
| 454,237 A | 6/1891 | Thomas |
| 4,116,564 A | 9/1978 | Renaud et al. |
| | (Continued) | |

FOREIGN PATENT DOCUMENTS

| | | |
|---|---|---|
| CN | 2128735 Y | 3/1993 |
| DE | 3338364 A1 | 5/1984 |
| | (Continued) | |

OTHER PUBLICATIONS

Baskurt, et al., "Cellular Determinants of Low-Shear Blood Viscosity", Biorheology, vol. 34, No. 3, 1977, pp. 235-247.
(Continued)

*Primary Examiner* — Rosanne Kosson
(74) *Attorney, Agent, or Firm* — Adler Pollock & Sheehan P.C

(57) ABSTRACT

The present invention generally relates to an apparatus, method, system for the determination of the aggregation rate of red blood cells. More specifically, the invention concerns a method, system, and the relative apparatus used to determine the aggregation rate of red blood cells, and other parameters related to these, such as viscosity, deformability, elasticity, density, in the field of in vitro medical analyses, using optical systems after or during inducted forces for red blood cell disruption and redistribution generated by ultrasound waves.

10 Claims, 1 Drawing Sheet

Related U.S. Application Data continuation of application No. 15/003,272, filed on Jan. 21, 2016, now Pat. No. 9,696,293, which is a continuation of application No. 14/176,307, filed on Feb. 10, 2014, now Pat. No. 9,279,800, which is a continuation of application No. 13/740,843, filed on Jan. 14, 2013, now Pat. No. 8,647,886.

(60) Provisional application No. 61/586,502, filed on Jan. 13, 2012.

(52) U.S. Cl.
CPC .. *G01N 33/4915* (2013.01); *G01N 2015/0073* (2013.01); *G01N 2015/0092* (2013.01)

(56) References Cited

U.S. PATENT DOCUMENTS

| | | | |
|---|---|---|---|
| 4,135,819 | A | 1/1979 | Schmid-Schonbein |
| 4,197,735 | A | 4/1980 | Munzer et al. |
| 4,201,470 | A | 5/1980 | Ehrly et al. |
| 4,352,557 | A | 10/1982 | Schmid-Schonbein et al. |
| 4,398,894 | A | 8/1983 | Yamamoto |
| 4,436,827 | A | 3/1984 | Tamagawa |
| 4,822,568 | A | 4/1989 | Tomita |
| 4,964,728 | A | 10/1990 | Kloth et al. |
| 5,071,247 | A | 12/1991 | Markosian et al. |
| 5,367,157 | A | 11/1994 | Nilsson et al. |
| 5,506,145 | A | 4/1996 | Bull et al. |
| 5,567,869 | A | 10/1996 | Rauch et al. |
| 5,827,746 | A | 10/1998 | Duic |
| 5,914,242 | A | 6/1999 | Honkanen et al. |
| 6,204,066 | B1 | 3/2001 | Wardlaw |
| 6,336,358 | B1 | 1/2002 | Kishimori et al. |
| 6,342,391 | B1 | 1/2002 | Chen et al. |
| 6,514,766 | B2 | 2/2003 | Spilled et al. |
| 6,531,321 | B1 | 3/2003 | Ryan et al. |
| 6,632,679 | B1 | 10/2003 | Breda |
| 6,711,424 | B1 | 3/2004 | Fine et al. |
| 6,974,701 | B2 | 12/2005 | Bouboulis |
| 7,005,107 | B2 | 2/2006 | Breda |
| 7,030,781 | B2 | 4/2006 | Jones |
| 7,043,289 | B2 | 5/2006 | Fine et al. |
| 7,202,939 | B2 | 4/2007 | Gui et al. |
| 7,207,939 | B2 | 4/2007 | Husher |
| 7,317,939 | B2 | 1/2008 | Fine et al. |
| 7,541,191 | B2 | 6/2009 | Duic |
| 7,833,489 | B2 | 11/2010 | Chen |
| 8,460,938 | B2 | 6/2013 | Forsell |
| 8,647,886 | B1 | 2/2014 | Sacchetti et al. |
| 9,110,031 | B2 | 8/2015 | Counord et al. |
| 9,279,800 | B2 | 3/2016 | Sacchetti et al. |
| 2009/0193878 | A1 | 8/2009 | Ciotti et al. |

FOREIGN PATENT DOCUMENTS

| | | | |
|---|---|---|---|
| EP | 0414223 | A2 | 2/1991 |
| EP | 0529420 | A2 | 3/1993 |
| EP | 0732576 | A1 | 9/1996 |
| KR | 20050014040 | A | 2/2005 |
| KR | 100871297 | B1 | 12/2008 |
| WO | 2004063722 | A1 | 7/2004 |
| WO | 2008072870 | A1 | 6/2008 |
| WO | 2009050757 | A2 | 4/2009 |

OTHER PUBLICATIONS

Baskurt, et al., "Comparison of Three Instruments for Measuring Red Blood Cell Aggregation", Clinical Hemorheology and Microcirculation, vol. 43, No. 4, 2009, pp. 283-298.
Baskurt, et al., "Red Blood Cell Aggregation", CRC Press, 2012.
Casey, et al., "Advanced Public Transportation Systems: The State of the Art", Component of Departmental IVHS Initiative, Apr. 1991, 96 pages.
Chen, et al., "Monitoring of Red Blood Cell Aggregability in a Flow-chamber by Computerized Image Analysis", Clinical Hemorheology, vol. 14, No. 4, 1994, pp. 497-508.
Collings, et al., "Ultrasonic Determination of Erythrocyte Derformability", Australasian Physical and Engineering Sciences in Medicine, vol. 5, No. 3, Jul. 1, 1982, pp. 98-101.
Davies, et al., "Assessment of Advanced Technologies for Transit and Rideshare Applications", Final Report, NCTRP Project 60-1A, Jul. 1991, 137 pages.
Dintenfass, "Erythrocyte Sedimentation Rates: A Tentative Correction for Haematocrit", Rheologica Acta, vol. 13, No. 6, 1974, pp. 936-943.
Extended European Search Report received in corresponding European Application No. 14737519.0, dated Nov. 18, 2015, 9 pages.
Fabry, "Mechanism of Erythrocyte Aggregation and Sedimentation", Blood, vol. 70, No. 5, Nov. 1987, pp. 1572-1576.
Gilles, et al., "The French Experience with Automatic Vehicle Location in Urban Transportation Systems", Report Presented at the International Conference on Automatic Vehicle Location System, Sep. 19-21, 1988.
Hardeman, et al., "The Laser-Assisted Optical Rotational Cell Analyzer (LORCA) as Red Blood Cell Aggregometer", Clinical Hemorheology and Microcirculation, vol. 25, No. 1, Mar. 6, 2001, pp. 1-12.
Iolascon, et al., "Hereditary Spherocytosis: From Clinical to Molecular Defects", Haematologica, vol. 83, Mar. 1998, pp. 240-257.
Keidan, et al., "Effect of Polymerization Tendency on Haematological, Rheological and Clinical Parameters in Sickle Hell Anemia", British Journal of Haematology, vol. 71, No. 4, Apr. 1989, pp. 551-557.
Kenner, "The Measurement of Blood Density and Its Meaning", Basic Research in Cardiology, vol. 84, No. 2, Mar.-Apr. 1989, pp. 111-124.
Mullaney, et al., "Cell Sizing: A Light Scattering Photometer for Rapid Volume Determination", Review of Scientific Instruments, vol. 40, Issue 8, 1969, pp. 1029-1032.
International Search Report and Written Opinion received in Corresponding International Application No. PCT/US2014/011095, dated May 7, 2014, 5 pages.
Plebani, et al., "The Test 1 Automated System: A New Method for Measuring the Erythrocyte Sedimentation Rate", Am. J. Clin. Pathol, vol. 110, 1998, pp. 334-340.
Potron, et al., "Approach to Erythrocyte Aggregation Through Erythrocyte Sedimentation Rate: Application of a Statistical Model in Pathology", vol. 36, No. 3, 1994, pp. 241-247.
Priezzhev, et al., "Aggregation and Disaggregation of Erythrocytes in Whole Blood: Study by Backscattering Technique", Journal of Biomedical Optics,vol. 4, No. 1, Available online at https://doi.org/10.1117/1.429923, Jan. 1999, pp. 76-84.
Shin, et al., "A Noble RBC Aggregometer With Vibration-Induced Disaggregation Mechanism", Korea-Australia Rheology Journal, vol. 17, No. 1, Mar. 2005, pp. 9-13.
Shin, et al., "Light-Transmission Aggregometer Using a Vibration-Induced Disaggregation Mechanism", Review of Scientific Instruments, vol. 76, Issue 1, Available online at https://doi.org/10.1063/1.1832456, 2005, pp. 016107-1-016107-3.
Tomita, et al., "Aggregation and Desaggregation as an Indication of Stop and Flow of Blood in a Tube and In Situ", Biorheology: The Official Journal of the International Society of Biorheology, vol. 18, No. 1, May 1981, p. 165.
Tomita, et al., "Whole-Blood Red Blood Cell Aggregometer for Human and Feline Blood", Am. J. Physiology Heart and Circulatory Physiology, Dec. 1986, pp. H1205-H1210.
Tse, et al., "Red Blood Cell Membrane Disorders", British Journal of Haematology, vol. 104, 1999, pp. 2-13.
Westergren, "On the Stability Reaction of the Blood in Pulmonary Tuberculosis", The British Journal of Tuberculosis, vol. 15, No. 2, 1921, pp. 72-76.
Zijlstra, "Syllectometry, A New Method for Studying Rouleaux Formation of Red Blood Cells", Netherlands Society for Physiology and Pharmacology. Proceedings, Groningen Session, Oct. 19, 1957.
Canada Office Action received for Canada Patent Application No. 2,935,839, dated Nov. 18, 2020, 4 pages.

(56) References Cited

OTHER PUBLICATIONS

Canada Office Action received for Canada Patent Application No. 2,935,839, dated Jan. 20, 2020, 5 pages.
Corrected Notice of Allowability received for U.S. Appl. No. 14/176,307, dated Feb. 19, 2016, 2 pages.
Corrected Notice of Allowability received for U.S. Appl. No. 14/176,307, dated Feb. 4, 2016, 3 pages.
Corrected Notice of Allowability received for U.S. Appl. No. 15/003,272, dated Apr. 5, 2017, 4 pages.
Corrected Notice of Allowability received for U.S. Appl. No. 15/640,852, dated Sep. 5, 2019, 2 pages.
Decision to Refuse the Application issued in European Application No. 14737519.0, dated Nov. 14, 2017, 6 pages.
European Office Action issued in European Application No. 14737519.0, dated Aug. 29, 2016, 6 pages.
International Preliminary Report on Patentability received for PCT International Application No. PCT/US14/11095, dated Jul. 23, 2015, 5 pages.
Non-Final Office Action received for U.S. Appl. No. 14/176,307, dated Mar. 26, 2015, 9 pages.
Non-Final Office Action received for U.S. Appl. No. 15/003,272, dated Nov. 28, 2016, 12 pages.
Non-Final Office Action received for U.S. Appl. No. 15/640,852, dated Jan. 7, 2019, 7 pages.
Notice of Allowance received for U.S. Appl. No. 13/740,843, dated Oct. 10, 2013, 14 pages.
Notice of Allowance received for U.S. Appl. No. 14/176,307, dated Oct. 21, 2015, 11 pages.
Notice of Allowance received for U.S. Appl. No. 15/003,272, dated Mar. 1, 2017, 8 pages.
Notice of Allowance received for U.S. Appl. No. 15/640,852, dated Aug. 1, 2019, 9 pages.
Restriction Requirement received for U.S. Appl. No. 13/740,843, dated May 7, 2013, 7 pages.
Requirement received for U.S. Appl. No. 131740,843, dated Jun. 25, 2013, 8 pages.
Restriction Requirement received for U.S. Appl. No. 14/176,307, dated Dec. 9, 2014, 8 pages.
Restriction Requirement received for U.S. Appl. No. 15/003,272, dated Jun. 17, 2016, 8 pages.
Restriction Requirement received for U.S. Appl. No. 15/640,852, dated Oct. 25, 2018, 6 pages.
Summons to attend oral proceedings issued in European Application No. 14737519.0, dated Apr. 5, 2017, 8 pages.

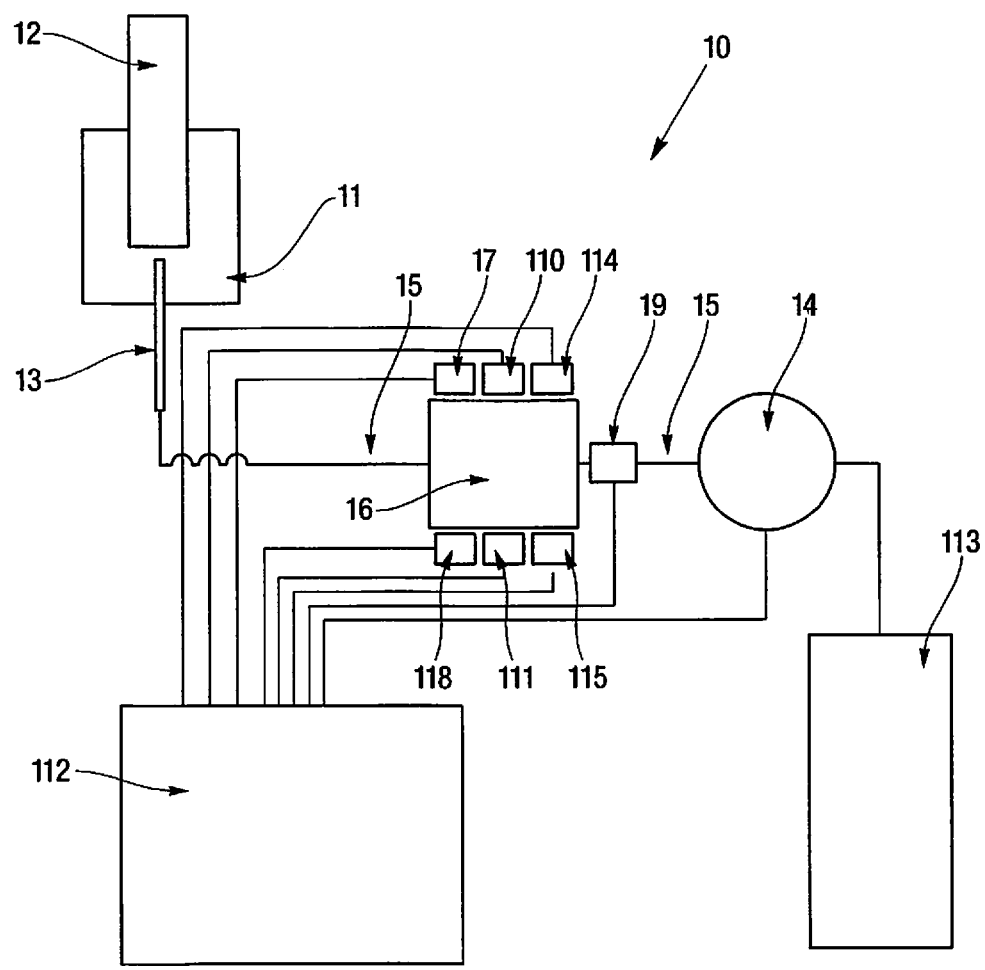

APPARATUS, METHOD, SYSTEM FOR THE DETERMINATION OF THE AGGREGATION RATE OF RED BLOOD CELLS

BACKGROUND

The subject technology generally relates to an apparatus, method, system for the determination of the aggregation rate of red blood cells. More specifically, the subject technology concerns a method, system, and the relative apparatus used to determine the aggregation rate of red blood cells, and other parameters related to these, such as viscosity, deformability, elasticity, density, in the field of in vitro medical analyses, using optical systems after or during inducted forces for red blood cell disruption and redistribution generated by ultrasound waves.

The state of the art for the determination of a test value corresponding to blood subsidence from an aggregogram or syllectogram of a blood sample is ascertained by reference to the article "Syllectometry, a new method for studying rouleaux formation of red blood cells" by Zijlstra published in 1963.

Aggregation is the first of three phases describing the sedimentation rate that is composed by: 1) Aggregation 2) Precipitation and 3) Packing. Erythrocyte Sedimentation Rate, which Westergren method is considered the gold standard method, is extensively used as a screening test for the determination of inflammatory status of a patient.

In the sedimentation phenomenon, aggregation is the first and the fastest among the three phases, which lasts less than two minutes, where red blood cells (RBC) forming chains (face to face aggregates) termed "Ruloux". This phase is reversible by mixing action, due, for example, with the repeated inversion of the test tube containing the sample. Rulouxformation causes are still not completely clear; the most important causes are related to proteins dispersed in plasma, such as fibrinogen. However, it is known that aggregation between RBC is strictly related to infections, inflammatory and connective tissue disorders.

A second stage aggregation phase, after Ruloux formation, spherical aggregates are formed between Ruloux with uniform increased mass, that sediment, after an initial acceleration, at constant speed conforming Stokes law. This second phase is called precipitation, and is the phase evaluated during the Westergren (WG) standard method.

As Stokes law describes that the constant speed is a balance between gravity force, viscosity and hydrostatic stress. The viscosity in a fluid as plasma is heavily affected by thermal effects and can modify sedimentation rate independently of the encountered Ruloux level. Also lipids dispersed in plasma, in conjunction with lipoproteins, can increase viscosity and reduce the precipitation phase and the resulting sedimentation rate measure.

Syllectometry is a measuring method that is commonly used to determine the red blood cell aggregability, which can be related to consequent sedimentation rate. As reference, in syllectometry light is incident to a layer where the sample is exposed to shear stress. Luminous flux attenuation/increase or backscatter ultrasound wave are used for determination of variations in sample density after the abrupt stop of driving mechanism. The subsequent time-dependent plot is called syllectogram.

Therefore, there remains a need in the prior art for an apparatus, method, system for the determination of the aggregation rate of red blood cells which does not require a stopped flow technique for aggregation kinetic detection.

BRIEF SUMMARY

The subject technology preserves the advantages of prior apparatus, methods, and systems for the determination of the aggregation rate of red blood cells. In addition, it provides new advantages not found in currently available apparatus, methods, and systems for the determination of the aggregation rate of red blood cells and overcomes many disadvantages of such currently available systems.

The subject technology generally relates to an apparatus, method, system for the determination of the aggregation rate of red blood cells. More specifically, the subject technology concerns a method, system, and the relative apparatus used to determine the aggregation rate of red blood cells, and other parameters related to these, such as viscosity, deformability, elasticity, density, in the field of in vitro medical analyses, using optical systems after or during inducted forces for red blood cell disruption and redistribution generated by ultrasound waves.

The subject technology provides a method and the relative reusable apparatus for the determination of aggregation rate index, and subsequent erythrocytes sedimentation rate for whole blood samples. The subject technology reduces the complexity of the pumping systems removing the need of the stopped flow condition. The subject technology provides other rheological parameters such as viscosity, deformability, elasticity, density. The subject technology provides a method and the relative apparatus for reducing the sample mixing time needed for the disruption of the aggregates RBC chains, using an alternative method prior and during the rheological behavior detection. The subject technology reduces the amount of sample volume needed for avoiding contamination by residuals of previous sample by applying an enhanced washing system.

BRIEF DESCRIPTION OF THE DRAWINGS

The novel features which are characteristic of the subject technology are set forth in the appended claims. However, the subject technology's preferred embodiments, together with further objects and attendant advantages, will be best understood by reference to the following detailed description taken in connection with the accompanying drawing in which:

FIG. 1 is a schematic view of an embodiment of the apparatus, method, and system for the determination of the aggregation rate of red blood cells.

DETAILED DESCRIPTION OF THE PREFERRED EMBODIMENTS

In accordance with the subject technology of FIG. 1, the subject technology generally relates to an apparatus, methods, and systems for the determination of the aggregation rate of red blood cells. More specifically, the subject technology performs a method used to determine the aggregation rate of red blood cells, and other parameters related to these, such as viscosity, deformability, elasticity, density, in the field of in vitro medical analyses, using optical systems after or during inducted forces for red blood cell disruption and redistribution generated by ultrasound waves.

The subject technology provides a method and the relative reusable apparatus for the determination of aggregation rate index, and subsequent erythrocytes sedimentation rate for whole blood samples. The subject technology reduces the complexity of the pumping systems removing the need of the stopped flow condition. The subject technology provides other rheological parameters such as viscosity, deformability, elasticity, density. The subject technology provides a method and the relative apparatus for reducing the sample mixing time needed for the disruption of the aggregates RBC chains, using an alternative method prior and during the rheological behavior detection. The subject technology reduces the amount of sample volume needed for avoid contamination by residuals of previous sample applying an enhanced washing system.

In one embodiment, the apparatus 10 for the determination of RBC aggregation, and their subsequent sedimentation rate, according to the subject technology comprises a reading cell container 16 where the sample is introduced. The apparatus 10 provides this reading cell container 16 equipped with two parallel optical windows for allowing light radiation to pass through the sample therein introduced or reading the backscatter of the incident light. The apparatus 10 comprises a collimated light source composed in such way that light passes through the windows of the container mentioned above, and can be reflected. On the opposite side of the light source 17, there is an optical detector 18 for the evaluation of the light attenuated by the sample. The optical detector 18 could be positioned on the same side of the light source 17 for the detection of light scattering. The reading cell container 16 is equipped with electromechanical actuators 110,111 able to vibrate the sample herein introduced, disrupting the aggregates naturally present in the blood sample, and evenly distributing the erythrocytes within the entire volume of sample. The apparatus has a temperature control system 114, 115 for the sample container to standardize the reaction environment.

The apparatus 10 comprises an electronic control device 112 able to acquire the optical variance detected by the optical detector, drive the electromechanical actuators 110, 111 and acquire the container temperature values. This electronic control device 112 is also able to convert the detected time dependent light variation into an aggregation index and the subsequent erythrocyte sedimentation rate, providing the result of the evaluated phenomenon in the way of a numerical result comparable to the commonly used parameters used in a clinical laboratory.

According to another embodiment of the subject technology, the apparatus or system 10 is comprised of a mixer device 11 for a low homogenization of the sample inside a collection tube 12. The homogenization can be achieved by a Vortex like mixer or by the radial or axial rotation of the sample tube.

After homogenization, the sample is then withdrawn by a needle 13 and aspirated by a pump device 14 through a hydraulic circuit 15. The hydraulic circuit 15 connects the aspiration needle 13 to the reading cell container 16 to allow their filling by the sample, guaranteed by the optical sensor composed by the emitter 17 and an optical receiver 18 and a secondary optical flow sensor 19 controlled by an electronic control device 112.

The light emitter source 17 is composed, in one embodiment, with a Light Emitting Diode (LED), and can be substituted, for example, by a laser source or an incandescent lamp. The optical receiver 18, in this embodiment, may include a CCD sensor for two dimensional characterization of the reaction. This sensor can be substituted with a single receiver element such as photodiode, photomulliplier etc.

After the complete or desired filling of the reading cell 16 the pump device 14 is stopped by the electronic control device 112, and the sample is processed by the electromechanical devices 110, 111, for example composed by piezoceramics, activated to a predetermined power by the control device 112, to disrupt aggregates and evenly re-suspend the RBC on the sample volume. A prerequisite for an aggregation kinetic detection is a complete disruption of the aggregates, normally formed in a steady state of the sample. This disruption can be achieved by an intensive mixing phase before and during the transportation of the sample in the reading cell or detection.

As an alternative to a predetermined power, the piezoceramic power is initially ramped up to a level where cell emulsification is detected through the optical reading. This process is stopped and a duplicate sample is introduced. The power applied can be optimized at a fraction of the emulsification power level which results in maximum dispersion, without cell damage.

During this phase the control device 112 acquires the signal detected by the optical receiver 18 and stops the electromechanical devices 110, 111 or actuators when the light variation detected by the receiver 18 stops decreasing, indicating the complete disruption of the aggregate present into the sample. This recorded plot expresses the disruption rate of the RBC and is post evaluated by the system.

In one embodiment, the shape of the reading cell container 16 walls comprises sound lenses for focusing the wave pressure shear to emphasize the shear inducted to the sample.

After the electromechanical devices 110,111 stop, the signal detected by the receiver 18 is still recorded by the control device 112 for a predetermined amount of time as a plot of kinetic aggregation.

After the end of the acquisition the sample is evacuated from the reading cell 16 by the pump device 14 to a waste reservoir 113. During the evacuation, the electromechanical devices 110, 111 are activated with a high power to remove proteins bonded to the walls of the reading cell container 16. An evacuation of the reading chamber avoids the pollution of the sample currently under measure by the residual of the previous measured sample with washing and does not require a large flow amount of sample currently under measure for removal the residuals of the previous measured sample. After the evacuation, the system is ready for a new sample and analysis.

The reading cell container 16 is also maintained to a controlled temperature by the thermoelectric device 114 and the temperature is acquired by the control device 112 through the temperature sensor 115 for providing standardized conditions of reaction.

During the dispersion phase induced by the electromechanical devices 110, 11, the resultant signal is evaluated to extract the mean viscosity value of the sample plasma by considering the time needed by the sample to completely re-suspend. After a complete re-suspension of the sample, a burst of ultrasound waves is induced to the sample for evaluating the red blood cell deformability. This deformability is considered as the time needed by the media to absorb the wave shear impressed, also decay after the wave share absorption is evaluated in function of time as index of the mean shape recovery ability.

It should be appreciated that the system, method, and apparatus may include one or more components or steps listed above in a variety of configurations depending upon desired performance or requirements.

It would be appreciated by those skilled in the art that various changes and modifications can be made to the illustrated embodiments without departing from the spirit of the subject

What is claimed is:

1. An apparatus comprising:
   (a) a mixer device configured for mixing a blood sample within a collection tube;
   (b) a needle configured for insertion within the collection tube for withdrawal of a portion of the blood sample, the needle connected to a hydraulic circuit for transporting the blood sample portion using a pump;
   (c) a reading cell container operationally connected to the hydraulic circuit configured for receipt of the blood sample portion;
   (d) a light emitter source positioned about the reading cell to pass light through the blood sample portion;
   (e) an optical receiver positioned opposite the light emitter source and about the reading cell to detect scattered light passing through the blood sample portion; and
   (f) a disruption mechanism connected to the reading cell container for disruption of the red blood cells within the blood sample portion to assist in recording the disruption rate.

2. The apparatus of claim 1 further comprising (g) a main controller operationally connected to the disruption mechanism, the main controller configured to activate the disruption mechanism for the disruption of the red blood cells within the blood sample portion until scattered light detected stops decreasing indicating the complete disruption of aggregates within the blood sample portion.

3. The apparatus of claim 2 further comprising (h) a fluid reservoir connected to the reading cell container for receipt of an evacuated blood sample portion from the reading cell container.

4. The apparatus of claim 3 further comprising (i) an evacuation mechanism to evacuate the blood sample portion from the reading cell container.

5. The apparatus of claim 4 wherein the evacuation mechanism is configured to provide ultrasound stress.

6. The apparatus of claim 1, wherein the reading cell container is non-disposable.

7. The apparatus of claim 2 wherein the reading cell container is configured for the optical detection of aggregation reaction.

8. The apparatus of claim 2 wherein the disruption mechanism is an actuator.

9. The apparatus of claim 2 wherein the disruption mechanism is an ultrasonic inducted mechanism for the disruption of red blood cells aggregates.

10. The apparatus of claim 2 wherein the disruption mechanism is electricity from a piezoceramic material which is initially ramped up to a level where cell emulsification is detected through the reading cell.

* * * * *